(12) United States Patent
Andre

(10) Patent No.: US 9,775,738 B2
(45) Date of Patent: Oct. 3, 2017

(54) NASAL DILATOR AND USE THEREOF

(71) Applicant: Robert Andre, Amsterdam/Durgerdam (NL)

(72) Inventor: Robert Andre, Amsterdam/Durgerdam (NL)

( * ) Notice: Subject to any disclaimer, the term of this patent is extended or adjusted under 35 U.S.C. 154(b) by 145 days.

(21) Appl. No.: 13/261,893

(22) PCT Filed: Nov. 13, 2012

(86) PCT No.: PCT/NL2012/000072
§ 371 (c)(1),
(2) Date: May 14, 2014

(87) PCT Pub. No.: WO2013/073934
PCT Pub. Date: May 23, 2013

(65) Prior Publication Data
US 2014/0296904 A1    Oct. 2, 2014

(30) Foreign Application Priority Data

Nov. 14, 2011 (NL) .................................. 1039165
Nov. 15, 2011 (NL) .................................. 1039166

(51) Int. Cl.
*A61F 5/08* (2006.01)
*A61F 5/56* (2006.01)
(Continued)

(52) U.S. Cl.
CPC .................. *A61F 5/08* (2013.01); *A61F 5/56* (2013.01); *A61B 17/24* (2013.01); *A61F 2/186* (2013.01)

(58) Field of Classification Search
CPC .... A61F 5/08; A61F 5/56; A61F 2/186; A61F 5/566; A61M 29/00; A61M 2210/0618;
(Continued)

(56) References Cited

U.S. PATENT DOCUMENTS 1,014,758 A * 1/1912 Knowlson ................. A61F 5/08
606/199
5,850,834 A 12/1998 Yoshida et al.
(Continued)

FOREIGN PATENT DOCUMENTS

CN    2681731 Y    3/2005
CN    2701419 Y    5/2005
(Continued)

*Primary Examiner* — Darwin Erezo
*Assistant Examiner* — Katherine Schwiker
(74) *Attorney, Agent, or Firm* — Shewchuk IP Services, LLC; Jeffrey D. Shewchuk

(57) ABSTRACT

A nasal dilator comprises magnets. The nasal dilator is a set comprising two bodies. Each of the two bodies has a first leg having at a distal portion thereof a magnet; and a second leg connected to the first leg via a bridge comprising flexible material. Each of the two bodies are designed so as to allow said body to be clamped to an ala nasi of a human nose between the distal portions of said first leg and said second leg. The magnets of the bodies are aligned such that with a body clamped to the ala nasi of a nose, the magnet is oriented at an angle to a plane defined by the ala nasi area clamped between said two distal portions of said first leg and second leg. Thanks to the repelling action of the magnets, the alae nasi are pushed apart, resulting in improved ease of breathing.

20 Claims, 8 Drawing Sheets

(51) Int. Cl.
*A61M 29/00* (2006.01)
*A61B 17/24* (2006.01)
*A61F 2/18* (2006.01)

(58) Field of Classification Search
CPC .............. A61B 17/24; A61B 2017/246; A61B 2017/248; A61B 2017/00867; A61N 2/00; A61N 2/06
USPC ....... 606/199; 128/848, 200.24, 858; 623/10
See application file for complete search history.

(56) References Cited

U.S. PATENT DOCUMENTS

| | | | | |
|---|---|---|---|---|
| 5,947,119 | A * | 9/1999 | Reznick | A61F 5/08 128/204.12 |
| 2004/0261791 | A1 * | 12/2004 | Horian | A61F 5/08 128/200.24 |
| 2009/0093840 | A1 * | 4/2009 | MacDonald | A61F 5/08 606/199 |
| 2010/0030252 | A1 * | 2/2010 | Stewart | A61F 5/08 606/199 |
| 2010/0125295 | A1 * | 5/2010 | Wien | A61F 5/08 606/196 |
| 2010/0331877 | A1 * | 12/2010 | Li | A61F 5/08 606/204.45 |
| 2011/0034950 | A1 * | 2/2011 | Toriumi | A61F 5/08 606/199 |
| 2011/0178545 | A1 * | 7/2011 | Gonzalez | A61B 17/24 606/201 |

FOREIGN PATENT DOCUMENTS

| | | |
|---|---|---|
| CN | 101264370 A | 9/2008 |
| CN | 201194868 Y | 2/2009 |
| DE | 3613736 A1 | 10/1986 |
| DE | 10 2005 021 239 A1 | 11/2006 |
| KR | 2008 0015736 A | 2/2008 |
| KR | 20080015736 * | 2/2008 |

* cited by examiner

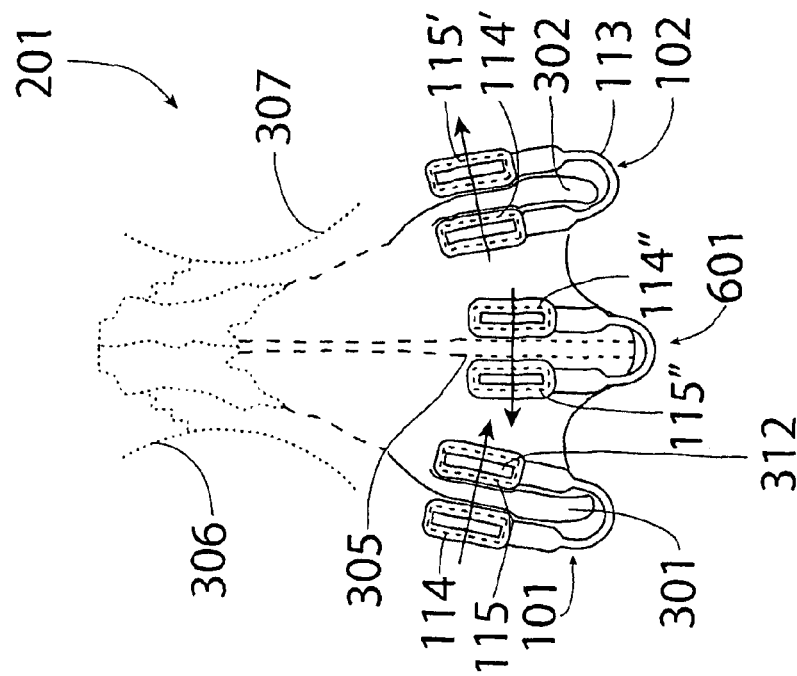
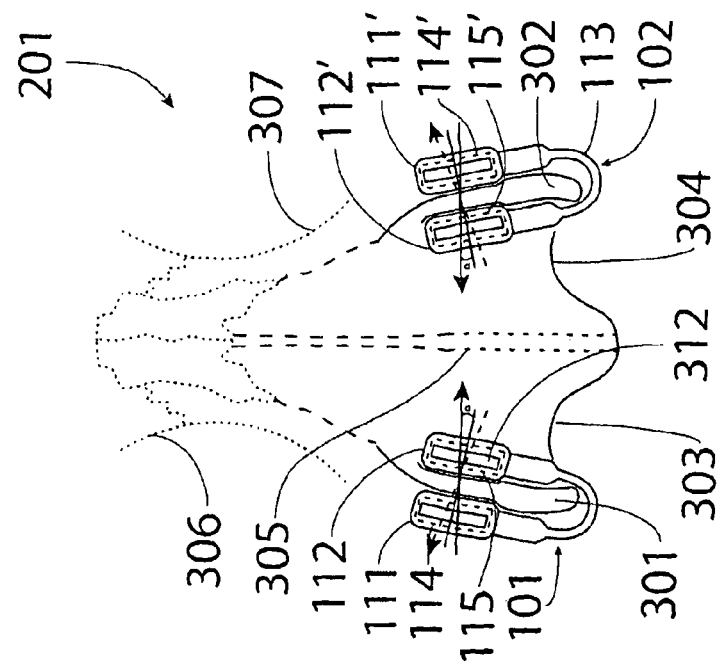
Fig. 6
Fig. 5

NASAL DILATOR AND USE THEREOF

The present invention relates to a nasal dilator comprising magnets.

A nasal dilator is a device for improving respiration through the nose. Nasal dilators are used to reduce discomfort due to a blocked nose, to reduce snoring, and to improve nasal airflow during sporting activities. For a normal person, about 50% of the total airway resistance is in the nose and the remainder in the lower airways. The nose has a constriction (bottleneck), usually located at the internal nasal valve area, that determines most of the airflow resistance in the nose. From the alar rims to the nasal bones, and therefore at the location of the constriction, the lateral walls of the nose are flexible. The restriction of the air flow through the nose exists in particular when inhaling. The reason for this is that because the lateral walls come closer together during inhalation, the constriction in the nose becomes more severe. A modest improvement in the cross-sectional flow-through area, effectively reducing the constriction in the nose, can make a significant difference in nasal airflow. This can be understood in view of Poiseuille's Law for the flow through tubes having a circular cross-section, which law shows that the resistance to flow is inversely related to the radius of such a tube to the power four.

Basically, there are two main types of nasal dilators: 1) Bandaid-like nasal dilators, which are single use (disposable). They comprise a resilient member attached to an adhesive base. The adhesive base is applied to the outside of the nose, bending the resilient member. Because the resilient member tries to revert to its original straight shape, the bandaid-like nasal dilator exerts an outward force on the lateral walls of the nose, widening the air passages in the nose. 2) Re-usable intra-nasal devices with two legs. The legs of the intra-nasal device are introduced in the nostrils, one leg in each nostril. The legs push away from each other, against the inner surface of the air passages in the nose. The force is exerted because the intra-nasal device comprises resilient material or oppositely oriented magnets are present at the distal portions of the legs.

The prior art is replete with patent applications for magnetic anti-snore devices that lack any physical basis, with a fictitious effect attributable to non-factual belief in magical properties of magnets. Examples of such publications are KR2008/0015736 (according to which the magnetism is delivered to the brain [0035]) and EP0013778. The devices of said two publications comprise a body having two legs each provided with a magnet and to achieve its purported effect the body is clamped to the nasal septum. A set comprising two bodies is not disclosed or suggested. The magnetic strength is insufficient for repelling (120 gauss on page 3 line 57 of EP0013778).

A proper nasal dilator according to the preamble is known from JP2002301153A.

A disadvantage of this re-usable intra-nasal dilator is that the user may lose it during his/her sleep or other activity because the process of dislodging is energetically favourable and that the nasal dilator is somewhat limited when it comes to reducing the airway resistance.

The object of the present invention is to provide a re-useable nasal dilator that allows for improved breathing by reducing the nasal airway resistance.

To this end, a nasal dilator according to the preamble is characterized in that the nasal dilator is a set comprising two bodies, each of the two bodies having a first leg having at a distal portion thereof a magnet; and
a second leg connected to the first leg via a bridge comprising flexible material, each of said two bodies capable of being clamped to an ala nasi of a human nose between the distal portions of said first leg and said second leg.

In a state where both bodies are clamped to a respective ala nasi, the bodies repel each, other and the airway resistance is reduced. Because of the two legs of a body only one leg is introduced intra-nasally, the intra-nasal airflow resistance is increased to a limited extent, the increase being overcome by the repelling force. Because of the relatively even thickness of the ala nasi, the dislodging process is not particularly energetically favourable, which aids in keeping the bodies in place, i.e. clamped to the alae nasi. Compared to some other non-magnetic nasal dilators known in the art, the central area of each of the nasal passages is relatively unobstructed. This results in a reduction of the air resistance and hence improved ease of breathing. The flexible material of the bridge is for example a resilient material, allowing the body to be clamped to an ala nasi. The length of a body of a nasal dilator according to the present invention measured along said body from the distal portion of the first leg to the distal portion of the second leg is in general 2.5 to 6 cm, preferably 3 to 5 cm. The total magnetic strength provided by a body is in practice equivalent to a magnet with a magnetic force (Fh) on an iron plate (Fe) between 10 Newton (=1.0 kg) and 50 Newton (=5.1 kg), preferably between 14 Newton (=1.4 kg) and 40 Newton (=4.1 kg). Total magnetic strength means the combined magnetic force of both legs of a body. In general, a set will be packaged and sold as a unitary package containing a single set. Examples of such a unitary package are a blister package, pot with screw cap or a box with a lid.

According to a possible embodiment the set comprises a third body having a first leg having at a distal portion thereof a magnet; and
a second leg connected to the first leg via a bridge comprising flexible material, said third body being designed so as to allow said third body to be clamped to a nasal septum of a human nose between the distal portions of said first leg and said second leg.

In use, the magnet of the third body will be aligned such that with the third body clamped to the nasal septum of a nose, the magnet of the third repels the first and second bodies clamped to the alae nasi. The third body results in a reduction of the distance between two repelling bodies, allowing stronger repelling force for a given magnet strength, and/or allowing for the use of cheaper, smaller or weaker magnets. The first, second and third bodies may be identical. Because the septum is relatively sensitive, particular care should be take to avoid discomfort for a user. If the third body is clamped to the septum by a magnet in each of the first leg (111) and second leg (112) of said third body, weaker magnets may be employed for the third body than for the first and second body.

According to a favourable embodiment, the second leg has at a distal portion thereof a magnet-attractable element.

The magnet-attractable element is for example a steel element. It helps to focus the magnetic field and hence increase the force with which the magnets of two opposite bodies of the nasal dilator attract. The use of a magnet-attractable element also helps to reduce, the risk that the magnet of the first leg (111) gets dislodged from the remainder of the body, which is undesirable as it might be inhaled by the user if the first leg (111) is inserted into the user's nostril.

According to a favourable embodiment, the magnet-attractable element is a magnetic element.

This allows for an even stronger increased repelling force. In contrast to the nasal dilator of JP2002301153A, part of the repelling force is generated outside the nose, thus less volume has to be occupied inside the nasal passages, thus increasing the ease of breathing.

According to a favourable embodiment, the bridge is a resilient bridge capable of exerting a force in a direction counteracting the magnetic attraction between the magnets of the first leg and the second leg.

The counteracting force does not prevent the bodies to be clamped to the ala nasi. The counteracting force allows to reduce discomfort to the wearer of the nasal dilator because the force with which the bodies clamp to the ala nasi is reduced (but still at a level where the bodies do not dislodge). In addition or alternatively, the strength of the magnets can be increased with the same comfort or reduced discomfort to the wearer, with further improved reduction of the nasal airways resistance. The bridge may have a U-shape and prevent opening of the U, which may help clamping the body to an ala nasi. Preferably, when a body is clamped to a plate (such as a plastic plate not interacting with the magnets) having a uniform thickness of 4 mm (chosen to be comparable to the average thickness of the ala nasi), the counteracting force is at least 25% of the force exerted by the magnets of the first and the second leg, and preferably at least 50%. This can be measured using a body lacking the magnets. Alternatively, this can be measured using weaker magnets (such as similar magnets but with reduced dimensions which may be obtained by cutting or grinding), in which case the counterforce will be able overcome the magnetic strength, that is, the body will not be able to clamp to the plate. To achieve the resilience, the bridge may contain a resilient element, such as a plastic element (e.g. as known from nasal dilator patches), for example of polypropylene or nylon. In addition or probably instead, the bridge may contain a notch or series of notches in the general direction of the width of the bridge. If the first leg and second leg are bent towards each other, this causes resilient bridge material adjacent to the notches to be compressed, resulting in the desired counter force.

According to a favourable embodiment, there is at least one notch over the width of the bridge with a first notch face and a second notch face, said notch faces contacting each other before the first leg and the second leg can touch by the magnetic force between the magnets of the first leg and the second leg.

This hampers the closing of the bodies, thus reducing the clamping force exerted by such a body. This helps to reduce discomfort to the wearer of the nasal dilator because the force with which the bodies clamp to the ala nasi is reduced (but still at a level where the bodies do not dislodge). In addition or alternatively, the strength of the magnets can be increased with the same comfort or reduced discomfort to the wearer, with further improved reduction of the nasal airways resistance. There will still be some flexibility left when the notch faces contact to accommodate for the varying thickness of the ala nasi between individuals.

According to a favourable embodiment, the magnetic strength of the magnet in the second leg is at least 25% more than the magnetic strength of the magnet in the first leg.

This makes it possible for a user of the nasal dilator to select the strength with which the bodies repel each other, by clamping the bodies either with their first legs inside the nasal passages or with the second legs inside the nasal passages. The magnets in the first leg (111) may be of a different magnetic material or grade thereof than the magnets of the second leg (112) and/or the difference in magnetic strength is the result of different dimensions of the magnets employed. E.g. the magnet in the second leg (112) may be thicker or composed of a stack of two magnets of the type used in the first leg (111).

According to a favourable embodiment, the bridge comprises a hinge allowing a body of the nasal dilator to clamp to a plate having a uniform thickness of 4 mm
  in a first position with sections of a first side of the body facing each other and
  in a second position with sections of a second side of the body facing each other, the second side being opposite to the first side, wherein the difference in distance between i) the magnet of the first leg, and ii) the magnet-attractable member in the second leg, in the first position and in the second position is at least 0.1 mm.

Depending on whether the bridge is given a U-shape by bending the legs in one way or the other way, the distal portions of the legs of the U-shaped body thus formed attract each other with a different force, and thus a user may select a clamping force comfortable for that user. The difference in distance between the magnets of the two legs is preferably at least 0.2 mm, more preferably at least 0.3 mm. It should be noted that the plate having a uniform thickness of 4 mm is not part of the nasal dilator and merely an aid for defining the embodiment.

According to a favourable embodiment, the magnet of a body is a planar magnet.

This reduces inconvenience for the user, because strong clamping can be achieved with limited force per unit of surface area. For a nasal dilator where the bodies each contain a magnet and a magnet-attractable element, the risk of dislodging the body is reduced. In general, the orientation of the magnetic field will be at an angle to the plane of said planar magnet, usually at an angle between 40° and 0° to the normal of the main plane.

According to a favourable embodiment, the magnet of a body is aligned such that the magnetic field is oriented at an angle $\alpha$ to the plane defined by the ala nasi area clamped between two distal portions, the angle $\alpha$ being between 5 and 15°.

This can be achieved using a magnet having a magnetic field at an angle to the normal of the main surface of the planar magnet, or a planar magnet with its main surface being at said angle to the plane defined by the ala nasi area clamped between said two distal portions of said first leg (111) and second leg (112). The former approach is preferable over the latter, because it allows for less volume being taken up by the intranasal portion of the body. The effect of the specified orientation is that in a first position of the bodies (e.g. with the first legs inserted into the nose) the magnetic fields of the first body and the second body repel each other with a stronger force than in a second position with the second legs inserted into the nose because the magnetic fields are then at an obtuse angle. This allows the user to select the force with which the bodies repel each other, even with identical magnets in the first and second leg (112). In the present application, the orientation of the magnet field is defined by a line through the south and north pole of the magnet.

According to a favourable embodiment, the legs and bridge of each body are made of flexible material, and the distal portion of at least one of the legs comprises a chamber for holding the magnet.

This reduces the chance that a magnet is dislodged from the leg.

According to a favourable embodiment, the flexible material is chosen from silicone and polyurethane.

These are relatively comfortable materials for a user. Their resilient nature can also contribute to retaining a magnet or magnet-attractable element in a leg.

According to a favourable embodiment, the nasal dilator comprises a bridging body comprising an elongated resilient member, the bridging body having a first distal portion and a second distal portion and a magnet attractable element at each of the first distal portion and the second distal portion.

Such a bridging body can be applied to the outside of the nose, bending the resilient member. It remains in place thanks to the magnet-attractable elements. Because the resilient member tries to revert to its original straight shape, the bridging body exerts an outward force on the lateral walls of the nose, widening the air passages in the nose.

Finally, the present invention relates to the use of a nasal dilator, wherein a set according to any of the preceding claims is used for improving nasal breathing for a therapeutic or non-therapeutic purpose.

Important non-therapeutic purposes are sports, such as performed by professional athletes. Therapeutic purposes included sleep apnea, and snoring.

The present invention will now be illustrated with reference to the drawing where FIG. 1 shows a top view on a nasal dilator according to the invention;

FIG. 2 shows a side view of a face of a user of the nasal dilator;

FIG. 3 a frontal, cut-out view of a nose provided with a nasal dilator;

FIG. 5 shows a frontal, cut-out view of a nose provided with a nasal dilator;

Figure 3:
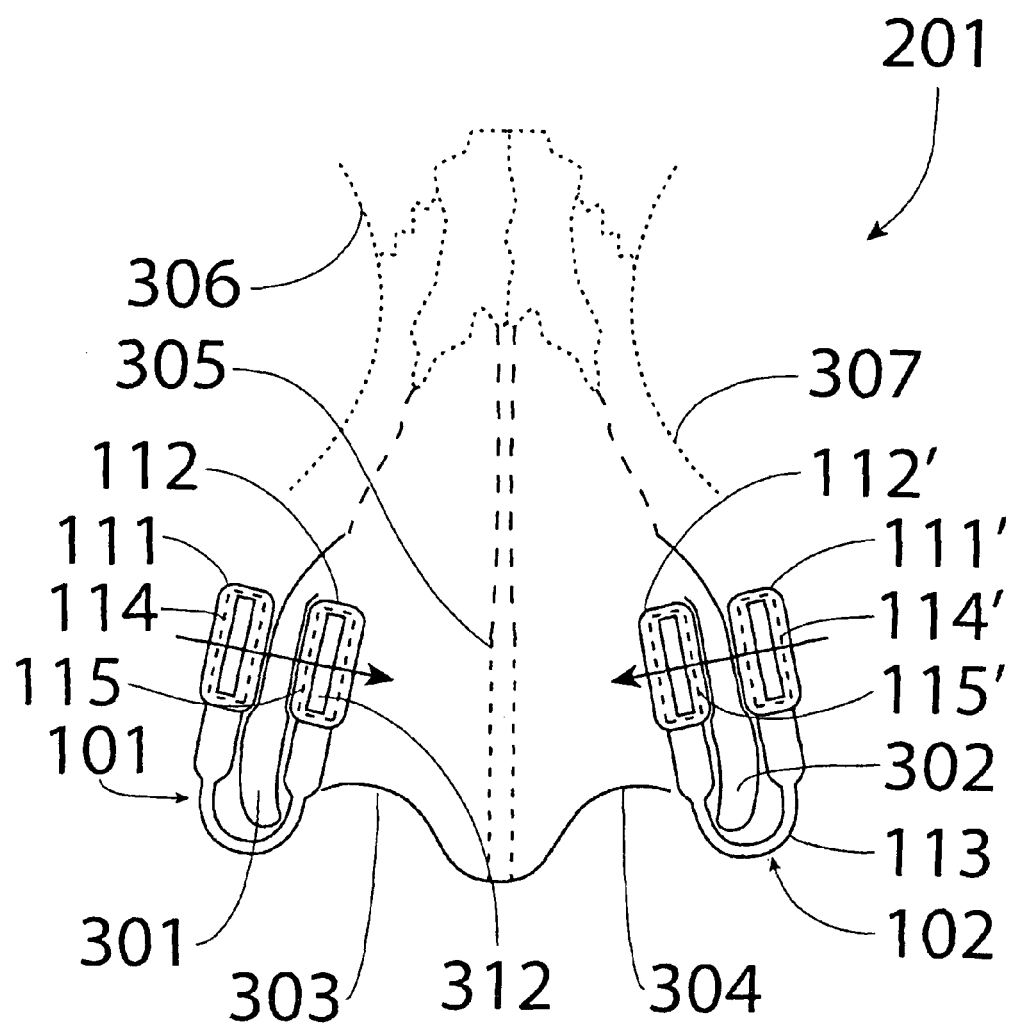
Figure 7:
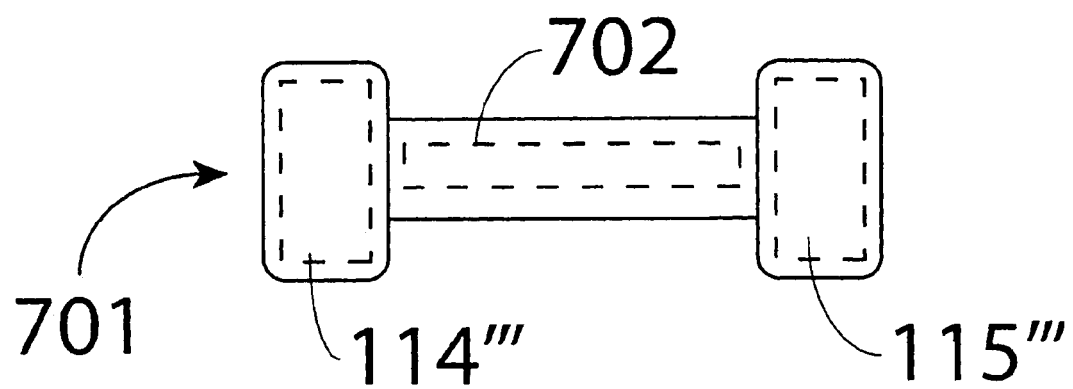
Figure 8:
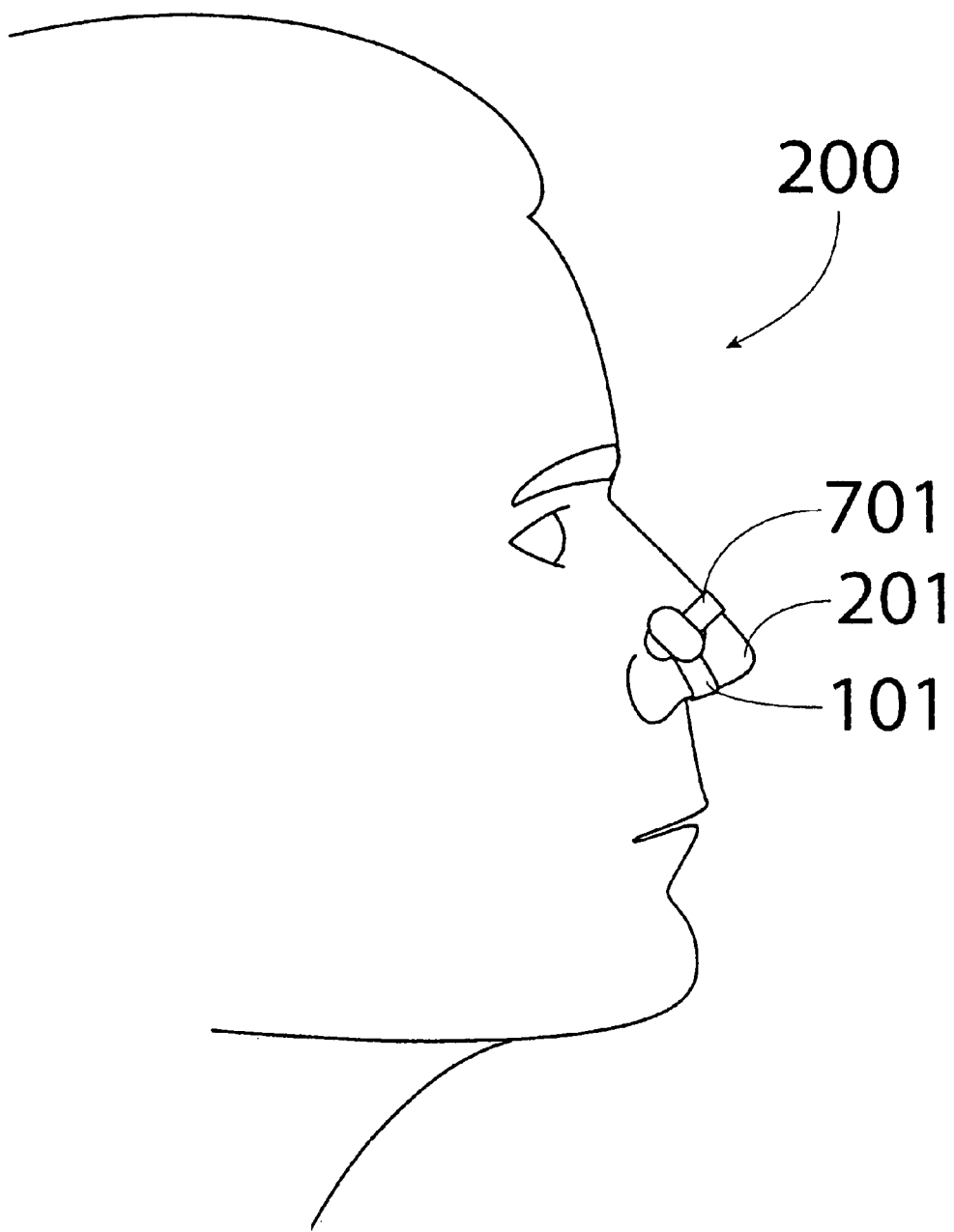
Figure 9A:
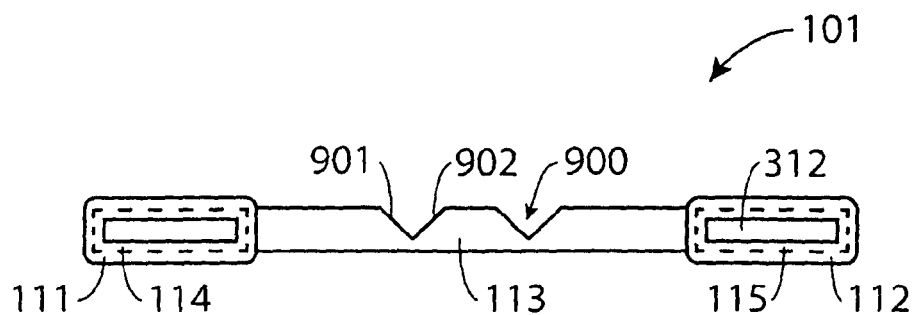
Figure 9B:
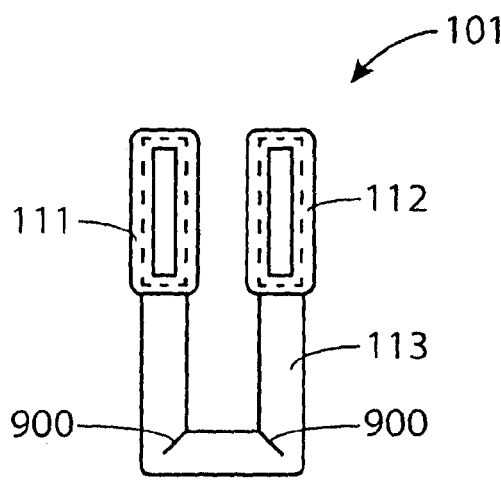
Figure 10:
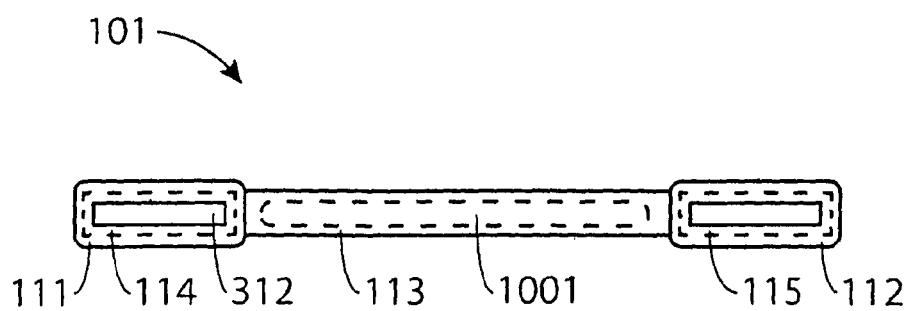

FIG. 6 corresponds with FIG. 3 and shows a nasal dilator comprising a third body;

FIG. 7 shows a bridging body of a nasal dilator according to the invention;

FIG. 8 shows a side view of a face of a user of the nasal dilator with the bridging body of FIG. 7;

FIG. 9a shows an alternative body of a nasal dilator in a first position and FIG. 9b shows said alternative body in a second position; and FIG. 10 shows an alternative embodiment of a body of a nasal dilator according to the invention.

Figure 1:
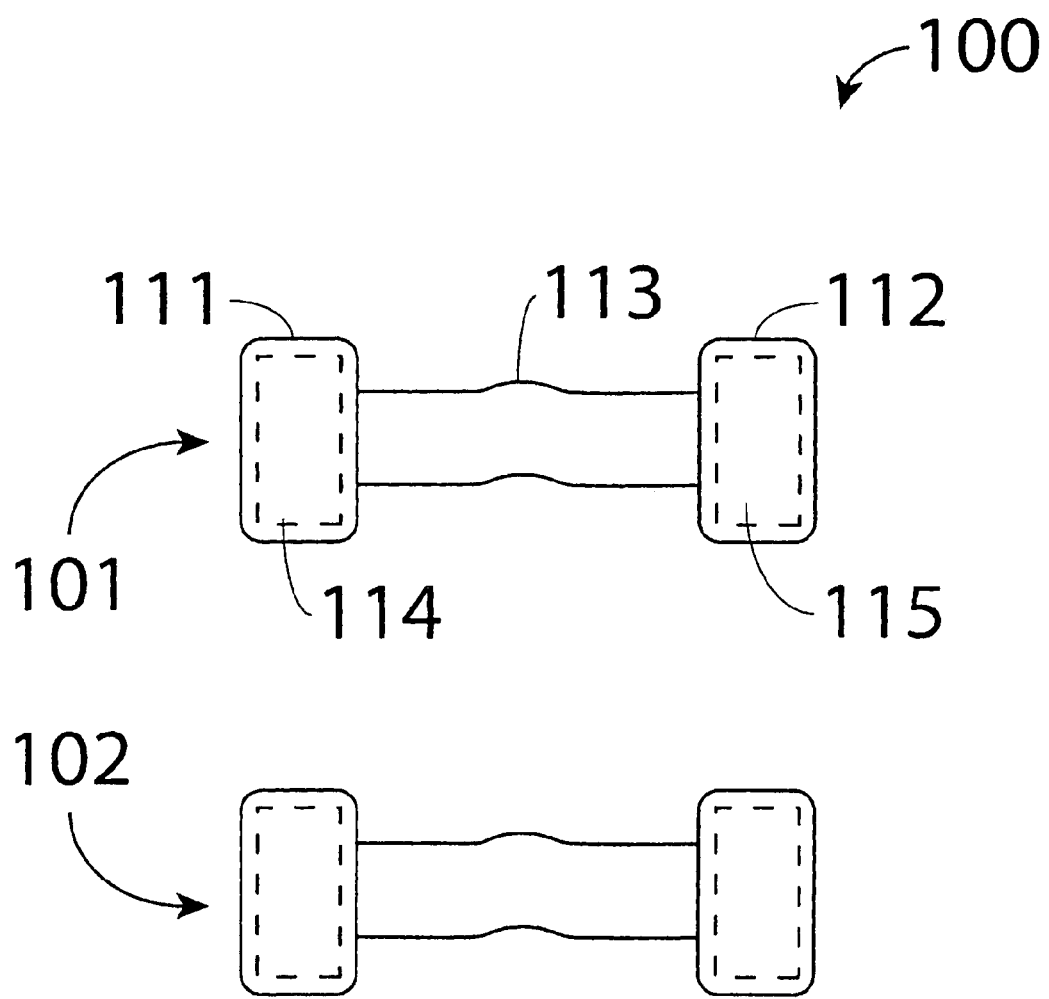

FIG. 1 shows a nasal dilator 100 comprising a first body 101 and a second body 102. The first body 101 and the second body 102 are made of flexible polyurethane (hardness: Shore A-70) and shown in an un-bent position of the bodies. The first body 101 comprises a first leg 111 and a second leg 112, joined via a bridge 113. At a distal portion of the first leg 111, the first leg 111 contains a first magnet 114. At a distal portion of the second leg 112, the second leg contains a second magnet 115. Of the first magnet 114 in FIG. 1 we face its south pole. Of the second magnet 115 we face its north pole.

Specifics of the magnets (Webcraft GmbH, Gottmadingen, Germany):
  Material: Neodymium (NdFeB)
  Coating: Gold-plated (Ni—Cu—Ni—Au)
  Measurements: length (l) 10 mm×width (w) 5 mm×height (h) 2 mm
  Magnet poles South/North over the height (h)=2 mm
  Max working temperature: 80° C.
  Material grade: N 50
  Magnetic flux density: 1.4 Tesla
  Magnetic force (Fh) on an iron plate (FE): 11.08 Newton=1.13 kg
  Dead weight: 0.76 g Experiments with bodies having one magnet in each leg showed magnets with a magnetic force (Fh) on an iron plate (Fe) between 7 Newton=0.7 kg and 20 Newton=2.03 kg to be effective. In experiments with weaker magnets the beneficial effect on the air flow increase was relatively limited while stronger magnets sometimes caused some discomfort. The magnets as specified above and used in the embodiment discussed here were effective and did not cause any significant discomfort.

Figure 2:
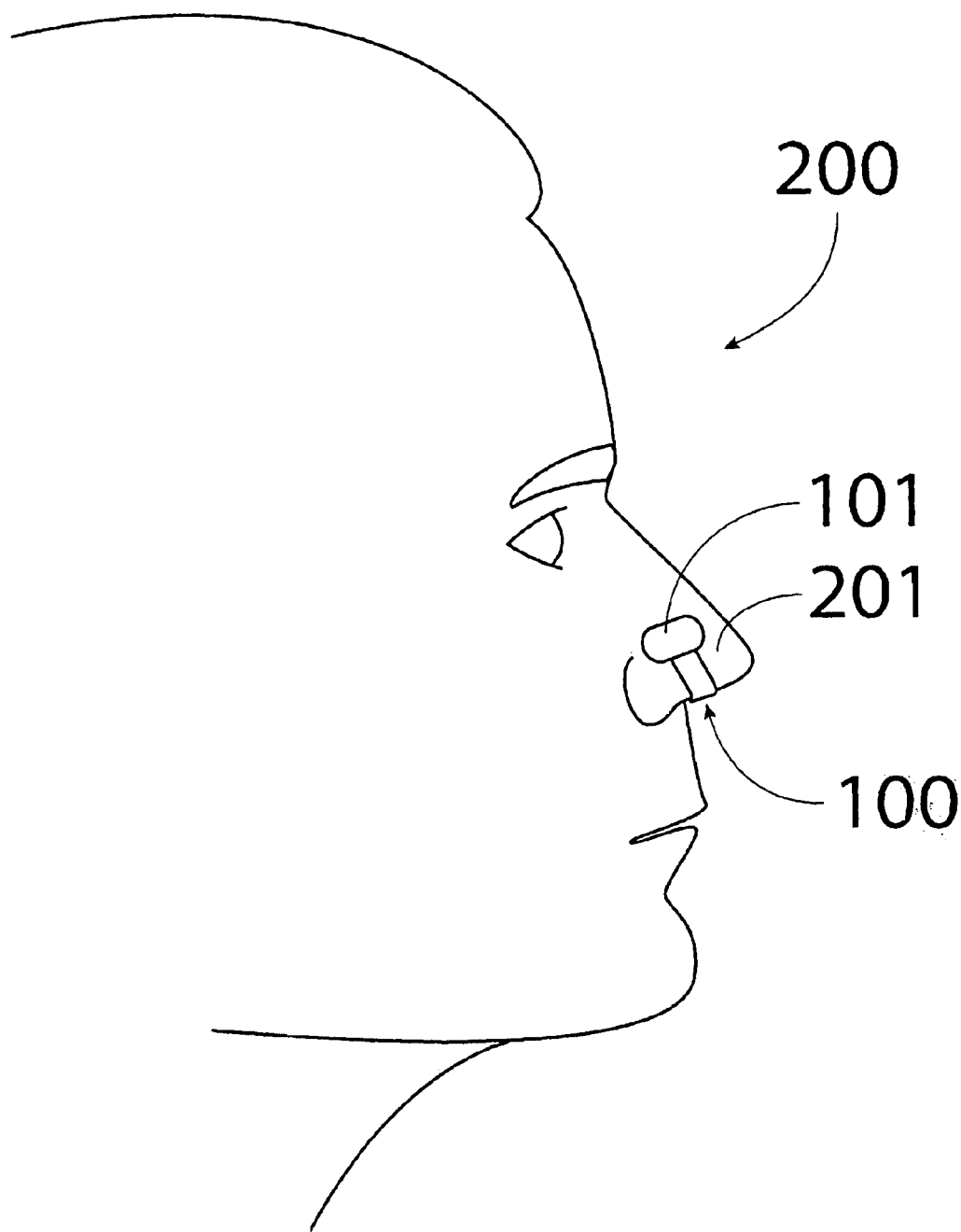

Dimensions of a body of the nasal dilator (un-bent):
  length from tip to tip: 36 mm
  width at the distal portion: 13 mm
  height at the distal portion: 8 mm
  thickness at the distal portion: 4.2 mm
  width of the legs: 6 mm
  thickness of the legs: 2 mm at the distal portion tapering towards the bridge 1 mm FIG. 2 shows a side view of a face 200 of a user of the nasal dilator 100, the user having a nose 201. Body 101 of the nasal dilator 100 is clamped to said nose 201.

FIG. 3 shows a frontal, cut-out view of the nose 201 which has two alae nasi 301, 302 left and right of nostrils 303, 304, the nostrils 303, 304 being left and right of nasal septum 305. For good measure, bony orbits 306, 307 for the right and left eye (not shown) have been indicated in part as well. Bone is shown in FIG. 3 with a dotted line.

First body 101 has been clamped to ala nasi 301 by inserting the second leg 112 of the first body 101 into nostril 303. Because the first magnet 114 at the distal portion of the first leg 111 of the first body 101 attracts the second magnet 115 at the distal portion of the second leg 112 of the first body 101, the first body 101 is securely clamped to the ala nasi 301 by the magnets. The alae nasi have a relatively constant thickness. As a result, a minor movement of a body clamped to an ala nasi is not significantly energetically different and the body does not become progressively more easily dislodged.

Second body 102 has been inserted with its second leg 112' in nostril 304 and clamped to the ala nasi 302 using magnets 114, 114'.

Because the north poles of the second magnets 115, 115' face each other, the bodies 101, 102 repel each other, widening the airway passages 311 inside the nose 201. This allows the user to inhale more easily and/or reduces snoring.

Because the first magnets 114 and the second magnet 115 of the first body 101 (and similarly for the second body) form a stack, the total magnetic strength with which the bodies 101, 102 repel each other is increased. So, the first magnets 114, 114' increase this repelling force without being present inside the nose 201. Being outside the nose 201, the first magnets 114, 114' do not reduce the cross-sectional flow-through area of the nasal airways 311 and consequently do not have a detrimental effect on the air flow resistance in the airway passages 311. The direction of the magnetic field has been indicated by arrows.

Dimensions of respective chambers in distal portions of the legs 111, 112 for holding the magnets:
  9.9×4.9×1.9 mm
Dimensions of slits 312 giving access to said chambers:
  3.7×0.7 mm While the bridge 113 is flexible, it is preferably not so flexible that it allows twisting over more than 90° as this may cause a leg to flip and then the magnet would be attracted to the opposite body.

Figure 4:
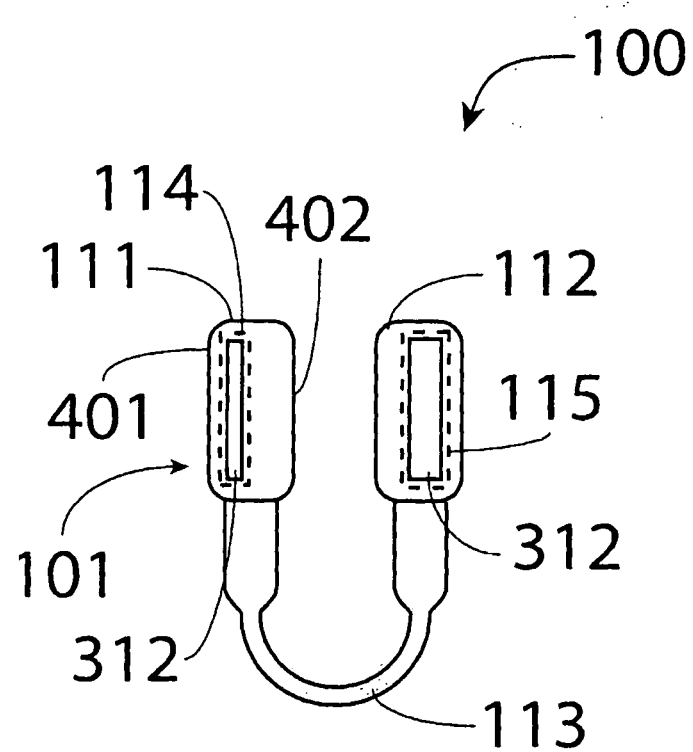
FIG. 4 shows a side view of a body of an alternative nasal dilator according to the invention in two positions.
Figure 4:
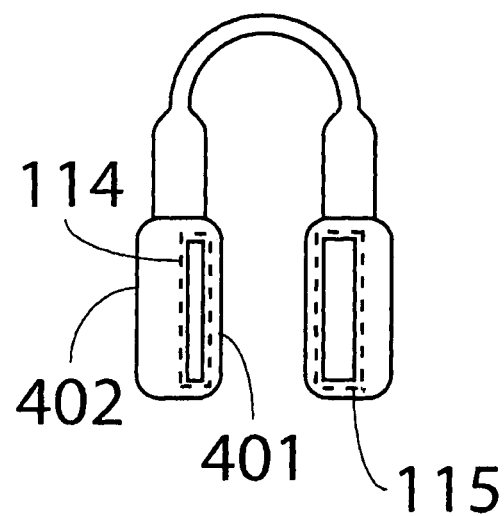

FIG. 4 shows a side view of a first body 101 of an alternative nasal dilator 100 bent in a first configuration (top) and bent in the opposite way in a second configuration (bottom). To allow body 101 to be in the first or second configuration as desired, in the embodiment discussed here the first leg 111, the second leg 112 and the bridge 113 are made of a flexible material, the bridge 113 having a thickness that is smaller than that of the first leg 111 and than the second leg 112.

The body 101 has a first side 401 and a second side 402. The first magnet 114 is closer to the first side 401 of body 101 than to the second side 402. The same goes for the second magnet 115 at the distal portion of the second leg 112. As a result, in the first configuration the first magnet 114 and the second magnet 115 are further apart than in the second configuration. Being further apart means that they don't attract each other as strongly in the first configuration as in the second configuration. As a result, the user can elect how strong the user wants to clamp the body 101 to the ala nasi 301 of his nose 201.

FIG. 4 also illustrates that the first magnet 114 may be of a different strength than the second magnet 115. In this embodiment, the first magnet 114 and the second magnet 115 are of the same material (neodymium), but second magnet 115 has twice the thickness. This can be easily achieved by stacking two magnets. The user may choose which leg of body 101 to insert into a nostril 303. Thus the user can choose how strong the bodies 101, 102 repel each other.

It is important to realise that this customization does not require any modification of the nasal dilator itself. It will be convenient if the first side 401 and the second side 402 are colour-coded, e.g. have a different colour or shade. This will make it easy to indicate the clamping strength. It will also be convenient if the first leg 111 has a different shape than the second leg 112. With a known shape, it is easy to insert either the first legs 111, 111' or the second legs 112, 112' into the nostrils 303, 304, depending on the desired strength with which the bodies 101, 102 repel each other.

In the embodiment of the first body 101 in FIG. 4, the magnets have been introduced in the distal portions of the legs via slits 312.

FIG. 5 corresponds to FIG. 3, except that the magnets have a magnetic field at an angle to the main surface of the respective magnet, in particular an angle α of 10° to the normal of the plane of the alae nasi 301, 302 and in a plane defined by the hinging bridge 113. As a result, the magnetic fields of the first bodies 101 and second body 102 are parallel and directly opposed (solid arrows). If the bodies are mounted with the second magnets at the outside of the nose, then magnetic fields (dotted arrows) are at an angle, and hence the first body 101 and the second body 102 do not repel each other as strongly.

FIG. 6 shows a frontal, cut-out view of the nose 201, corresponding to FIG. 3. A third body 601 has been clamped to septum 305, said third body 601 corresponding to the first body 101. The third body 601 comprises a first magnet 114" and a second magnet 115". Arrows indicate the way the bodies repel each other. In comparison to FIG. 3, the second body 102 has now been clamped to ala nasi 302 in the reverse orientation. Because the septum 305 is rather sensitive, the first magnet 114" and the second magnet 115" magnet may be weaker than the first and second magnets of the first body 101 and the second body 102.

FIG. 7 shows a bridging body 701 that corresponds to the first body 101 of FIG. 1 but differs from said first body 101 by the presence of an elongated resilient member 702, in itself known from bandaid-like nasal dilators. The bridging body 701 comprises magnet-attractable elements, such as a first magnet 114'" and a second magnet 115'".

The elongated resilient member 702 is straight, but when applied to the nose 201 as shown in FIG. 8 the elongated resilient member 702 is bent. It is stuck to the first body 101 and second body 102 (not visible) with the first magnet 114'" and the second magnet 115'". The bent elongated resilient member 702 wants to regain its straight shape, thus exerting a force on the alae nasi, bringing them further apart.

The use of a third body 601 and/or bridging body 701 have been disclosed as possibilities, but the use of more than two bodies is recognised as being more cumbersome for users. They do, however, allow for the use of weaker magnets, which may result in increased wearing comfort and/or the use of cheaper magnets.

FIG. 9a shows an alternative body 101 of a nasal dilator in a first position and FIG. 9b shows said alternative body 101 in a second position as it is used. The bridge 113 comprises at least one notch 900, and in the embodiment shown at two notches 900. Each notch has a first notch face 901 and a second notch face 902. In a folded stated, the second position shown in FIG. 9b), at least part of the faces contact each other, providing a counter force making it harder for the magnets 114 and 115 to come closer to the extent where it even may be impossible for the first leg 111 and the second leg 112 to touch each other (FIG. 9b), leaving a space of e.g. at least 2 mm. This reduces the force exerted on the ala nasi when such alternative bodies are clamped to the nose. The magnets 114, 115 may thus be very strong without much inconvenience to the user, allowing opposite bodies 101, 101' to repel each other more strongly, allowing even further improved breathing. The flexible nature of the bridge material and or the flexible nature of the bridge between a notch 900 and the most adjacent magnet ensure that the counter force is exerted over a range of angles, such that a counter force is also there if the legs 111, 112 are further apart, such as 5 mm apart. Thus a counterforce is provided for any person, irrespective of the thickness of their ala nasi.

The faces of the notches 900 are not necessarily flat but may be curved, are provided with protrusions or dams extending between opposite faces. This results in resilient material being progressively compressed, and thus a (progressive) counterforce over a sufficiently wide angle between the first and second leg to accommodate for the thickness of ala nasi of different people.

FIG. 10 shows an alternative body 101 of a nasal dilator having in the bridge 113 an elongated resilient member 1001, in itself known from bandaid-like nasal dilators. This helps to provide a counterforce to reduce the strength by which the magnets 114, 115 clamp to the ala nasi of a person. The magnets 114, 115 may thus be very strong, allowing opposite bodies 101, 101' to repel each other more strongly, allowing even further improved breathing.

The invention can be modified in various ways within the scope of the appended claims. For example, the magnets may have a hole and the legs may have a section with a reduction such that a magnet is held at the reduction. To prevent the magnet from rotating, the hole is preferably not round (if there is only one hole). A body may have a relatively rigid U-shape, i.e. a rigidity that prevents the legs from approaching each other under the influence of the magnets contained therein closer than 2 mm. For any of the subclaims 3 to 12, it is intended that the present invention covers a single body as well.

The invention claimed is:

1. A nasal dilator, wherein the nasal dilator is a set comprising two bodies, each of the two bodies having
   a first leg having at a distal portion thereof a first magnet with a first magnetic field of a first magnetic field strength; and
   a second leg connected to the first leg via a bridge comprising flexible material, the second leg having at a distal portion thereof a second magnet with a second magnetic field of a second magnetic field strength, the second magnetic field strength being weaker than the first magnetic field strength, with the first and second magnetic fields resulting in a combined magnetic field, each of said two bodies capable of being clamped to an ala nasi of a human nose with the ala nasi located between the distal portions of said first leg and said second leg, so that when the two bodies are used as a set on the human nose the combined magnetic field of the body on the right ala nasi opposes and repels the combined magnetic field of the body on the left ala nasi thereby pushing the alae nasi apart, resulting in widening of the nasal passages.

2. The nasal dilator according to claim 1, wherein the bridge is a resilient bridge exerting a force in a direction counteracting magnetic attraction between the first magnet of the first leg and the second magnet of the second leg.

3. The nasal dilator according to claim 1, wherein the bridge has a width, and wherein there is at least one notch over the width of the bridge with a first notch face and a second notch face, said notch faces contacting each other before the first leg and the second leg can touch by magnetic force between the first magnet of the first leg and the second magnet of the second leg.

4. The nasal dilator according to claim 1, wherein the second magnetic field strength is at least 25% less than the first magnetic field strength.

5. The nasal dilator according to claim 1, wherein the bridge comprises a hinge allowing a body of the nasal dilator to clamp to a plate having a uniform thickness of 4 mm
   in a first position with sections of a first side of the body facing each other and
   in a second position with sections of a second side of the body facing each other, the second side being opposite to the first side,
wherein the difference in distance between i) the first magnet and ii) the second magnet, in the first position and in the second position is at least 0.1 mm.

6. The nasal dilator according to claim 1, wherein the first magnet is a planar magnet.

7. The nasal dilator according to claim 6, wherein the first magnet and the second magnet are aligned such that the combined magnetic field is oriented at an angle $\alpha$ to a plane defined by the ala nasi area clamped between two distal portions, the angle $\alpha$ being between 5 and 15°.

8. The nasal dilator according to claim 1, wherein the legs and bridge of each body are made of flexible material, and the distal portion of the first leg comprises a chamber for holding the first magnet.

9. The nasal dilator according to claim 8, wherein the flexible material is chosen from silicone and polyurethane.

10. The nasal dilator of claim 1, wherein the first magnetic field strength is equivalent to a magnet with a magnetic force on an iron plate of at least 7 Newtons.

11. The nasal dilator according to claim 10, wherein a magnetic flux density of the magnet in the first body is at least 0.88 Tesla, and wherein a magnetic flux density of the magnet in the second body is at least 0.88 Tesla.

12. The nasal dilator according to claim 10, wherein the bridge of the first body biases the second leg away from the first leg while being clamped on the left ala nasi, and wherein the bridge of the second body biases the second leg away from the first leg while being clamped on the right ala nasi.

13. The nasal dilator according to claim 1, wherein the combined magnetic field has a strength equivalent to a magnet with a magnetic force on an iron plate of at least 7 Newtons.

14. The nasal dilator according to claim 1, wherein a magnetic flux density of the combined magnetic field is at least 0.88 Tesla.

15. The nasal dilator of claim 1, wherein the first magnet is a coated neodymium (NdFeB) magnet.

16. The nasal dilator of claim 1, wherein the second magnet is formed of steel.

17. A nasal dilator, wherein the nasal dilator is a set comprising two bodies, each of the two bodies having
   a first leg having at a distal portion thereof a first magnet having a magnetic field of a first magnetic field strength; and
   a second leg connected to the first leg via a bridge comprising flexible material, the second leg having at a distal portion thereof a magnet-attractable element formed of metal, the metal magnet-attractable element having a second magnetic field of a second magnetic field strength, the second magnetic field strength being weaker than the first magnetic field strength, with the first and second magnetic fields resulting in a combined magnetic field,
each of said two bodies capable of being clamped to an ala nasi of a human nose between the distal portions of said first leg and said second leg, so that when the two bodies are used as a set on the human nose the combined magnetic field of the body on the right ala nasi opposes and repels the combined magnetic field of the body on the left ala nasi thereby pushing the alae nasi apart, resulting in widening of the nasal passages.

18. The nasal dilator according to claim 17, wherein the first magnetic field strength of the first magnet is equivalent to a magnet with a magnetic force on an iron plate of at least 7 Newtons.

19. The nasal dilator according to claim 17, wherein a magnetic flux density of the first magnet is at least 0.88 Tesla.

20. The nasal dilator of claim 17, wherein the metal magnet-attractable element is formed of steel.

* * * * *